United States Patent [19]

Chen

[11] Patent Number: 5,591,131
[45] Date of Patent: Jan. 7, 1997

[54] SAFETY MINUTE DOSE HYPODERMIC SYRINGE

[76] Inventor: Long-Hsiung Chen, 5F, No. 91-3, Chung Cheng Rd., Sec. 1, Taipei, Taiwan

[21] Appl. No.: 547,365

[22] Filed: Oct. 24, 1995

[51] Int. Cl.⁶ .................................................. A61M 5/32
[52] U.S. Cl. .................................. 604/110; 604/195
[58] Field of Search ................................ 604/110, 187, 604/192, 195, 263, 218, 207

[56] References Cited

U.S. PATENT DOCUMENTS

| | | | |
|---|---|---|---|
| 4,728,320 | 3/1988 | Chen | 604/110 |
| 4,747,830 | 5/1988 | Gloyer et al. | 604/198 X |
| 4,770,655 | 9/1988 | Haber et al. | 604/110 |
| 5,295,973 | 3/1994 | Chen | 604/195 |

*Primary Examiner*—John D. Yasko
*Attorney, Agent, or Firm*—Bacon & Thomas

[57] ABSTRACT

A safety minute dose hypodermic syringe which includes a locating stopper mounted inside the front end of the barrel and connected to the locking tip, which holds the needle cannula, and an arrowhead-like retainer rod fixed secured to the movable rubber stopper and connected to the plunger, the arrowhead-like retainer rod being forced into engagement with an arrowhead-like retaining hole on the locating stopper after the injection, for permitting the locating stopper and the locking tip with the needle cannula to be pulled backwards by the plunger to the inside of the barrel and retained in place by inside annular flanges of the barrel, and for permitting the needle cannula to be deformed by the plunger when the plunger is disconnected from the retainer rod and inserted into the front end of the barrel.

5 Claims, 4 Drawing Sheets

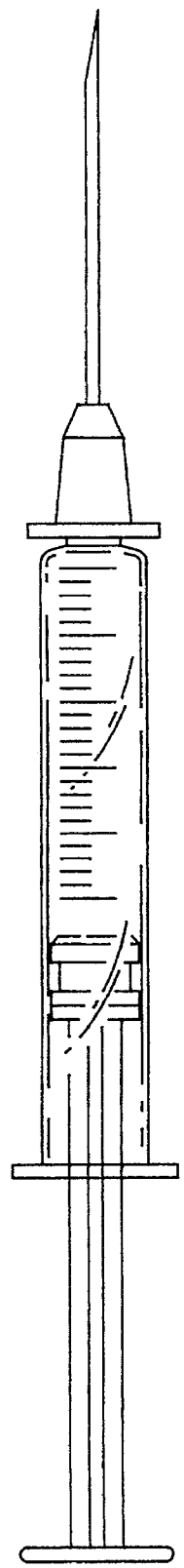
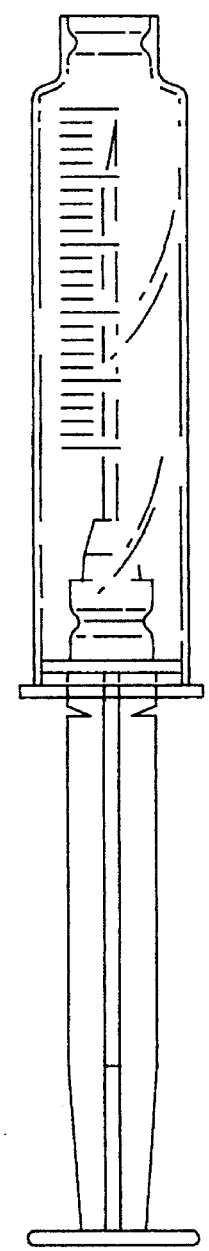
FIG. 1
(PRIOR ART)
FIG. 2
(PRIOR ART)

SAFETY MINUTE DOSE HYPODERMIC SYRINGE

BACKGROUND OF THE INVENTION

The present invention relates to minute dose hypodermic syringes, and relates more particularly to a safety minute dose hypodermic syringe which permits the needle cannula to be pulled back inside the barrel after the injection, and then deformed by the plunger by removing the plunger out of the rear end of the barrel and then inserting it into the front end of the barrel.

In order to prevent contamination, regular hypodermic syringes are commonly made disposable. FIG. 1 shows a regular minute dose hypodermis syringe which is generally comprised of a barrel, a locking tip fixedly secured to the front end of the barrel on the outside to hold a needle cannula, and a plunger having a front end coupled with a rubber stopper moved in the barrel. The needle cannula must be damaged by a syringe crusher or the like after the injection, to prevent possible contamination. FIG. 2 shows a safety minute dose hypodermic syringe according to the prior art in which the locking tip is coupled to the front end of the plunger. After the injection, the plunger is pulled backwards to move the needle cannula to the inside of the barrel, and then the front end of the plunger is broken and retained on the inside of the barrel. However, because the needle cannula is still maintained intact, it may injure someone when the barrel is broken.

SUMMARY OF THE INVENTION

The present invention has been accomplished to provide a safety minute dose hypodermic syringe which permits the needle cannula to be received inside the barrel and then deformed after the use of the syringe. According to one aspect of the present invention, the safety minute dose hypodermic syringe comprises a locating stopper mounted inside the front end of the barrel and connected to the locking tip, which holds the needle cannula, and an arrowhead-like retainer rod fixed secured to the movable rubber stopper and connected to the plunger, the arrowhead-like retainer rod being forced into engagement with an arrowhead-like retaining hole on the locating stopper after the injection, for permitting the locating stopper and the locking tip with the needle cannula to be pulled backwards by the plunger to the inside of the barrel. According to another aspect of the present invention, the barrel has a first inside annular flange at the front end for holding the locking tip in the working position, a second inside annular flange and a third inside annular flange at the rear end for holding the locking tip with the needle cannula inside the barrel. According to still another aspect of the present invention, the plunger can be disconnected from the retainer rod by breaking the retainer rod, and then inserted into the barrel from its front end to deform the needle cannula.

BRIEF DESCRIPTION OF THE DRAWINGS

FIG. 1 shows a minute dose hypodermic syringe according to the prior art;

FIG. 2 shows another structure of minute dose hypodermic syringe according to the prior art;

DETAILED DESCRIPTION OF THE PREFERRED EMBODIMENT

Figure 3:
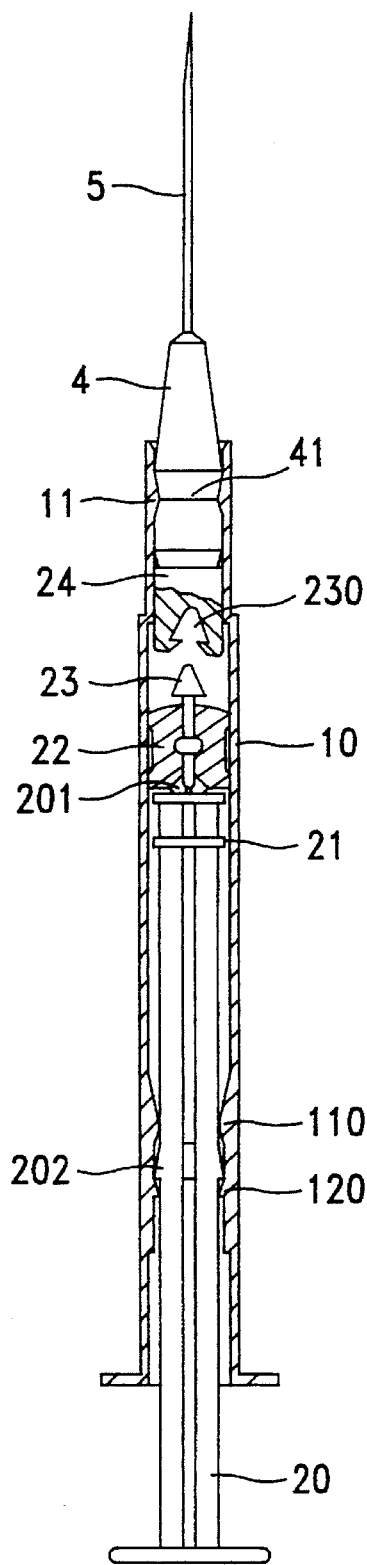
FIG. 3 is a longitudinal view in section of a safety minute dose hypodermic syringe according to the present invention.

Referring to FIG. 3, a safety minute dose hypodermic syringe in accordance with the present invention is generally comprised of a stepped barrel 10, a plunger 20, a locking tip 4 fastened to the front end of the stepped barrel 10, and a needle cannula 5 fastened to the locking tip 4 outside the stepped barrel 10. A locating stopper 24 is mounted inside the stepped barrel 10 and fixedly secured to one end of the locking tip 4 remote from the needle cannula 5, having a conical retaining hole 230 at one end remote from the locking tip 4. The conical retaining hole 230 slightly slopes in one direction from the longitudinal center axis of the locating stopper 24 and is disposed in communication with the needle cannula 5 for delivery of liquid medicine. The stepped barrel 10 comprises a first inside annular flange 11 near the front end, a second inside annular flange 110 and a third inside annular flange 120 near the rear end. The inner diameter of the front end of the stepped barrel 10 is relatively smaller than that of the rear end thereof. When the locking tip 4 is fastened to the front end of the stepped barrel 10, the first inside annular flange 11 of the stepped barrel 10 engaged an annular locating groove 41 around the periphery of the locking tip 4. The plunger 20 is inserted into the stepped barrel 10, having two collars 21 around the periphery near the front end, and a tapered flange 202 around the periphery in the middle. A movable rubber stopper 22 is inserted into the stepped barrel 10 to hold an arrowhead-like retainer rod 23. The arrowhead-like retainer rod 23 has a front end extended out of the movable rubber stopper 22, and a rear end connected to the front end of the plunger 20. The arrowhead-like retainer rod 23 further has a breaking neck 201 adjacent to the plunger 20.

Figure 4:
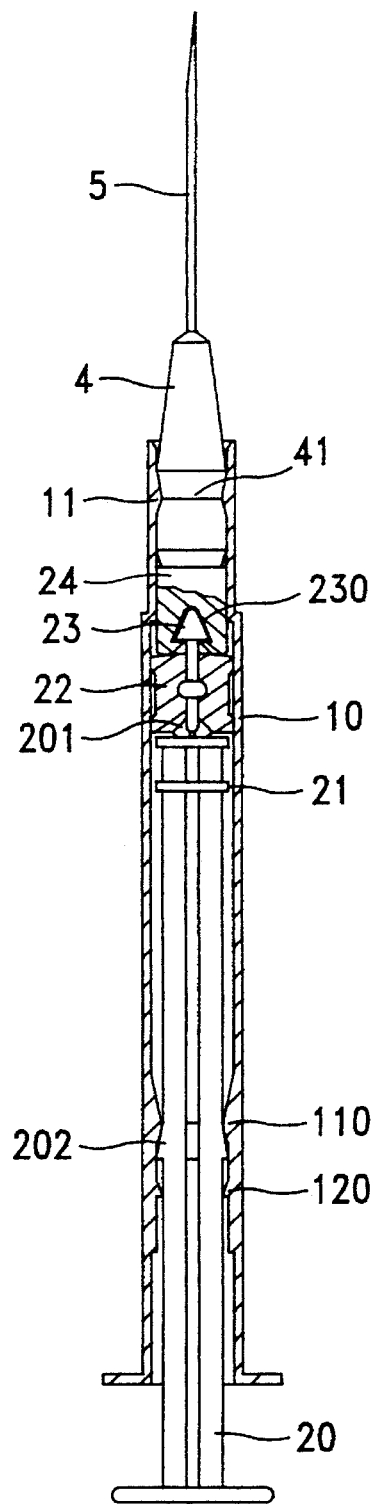
FIG. 4 is similar to FIG. 3 but showing the plunger moved to the front limit, and the retainer rod forced into engagement with the retaining hole of the locating stopper.
Figure 5:
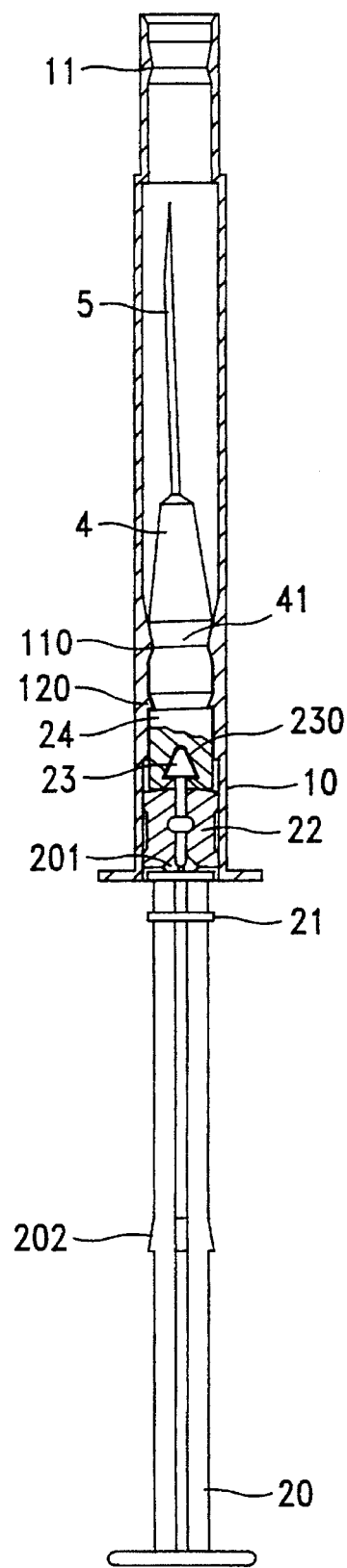
FIG. 5 shows the plunger moved backwards, and the locking tip with the needle cannula received inside the barrel according to the present invention.
Figure 6:
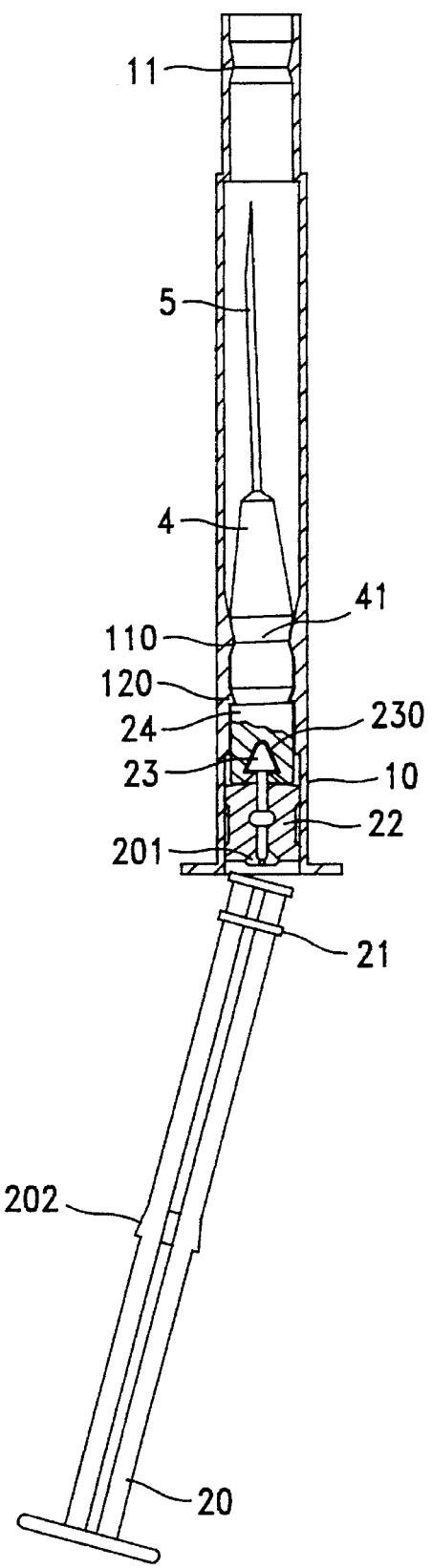
FIG. 6 shows the plunger disconnected from the retainer rod according to the present invention.
Figure 7:
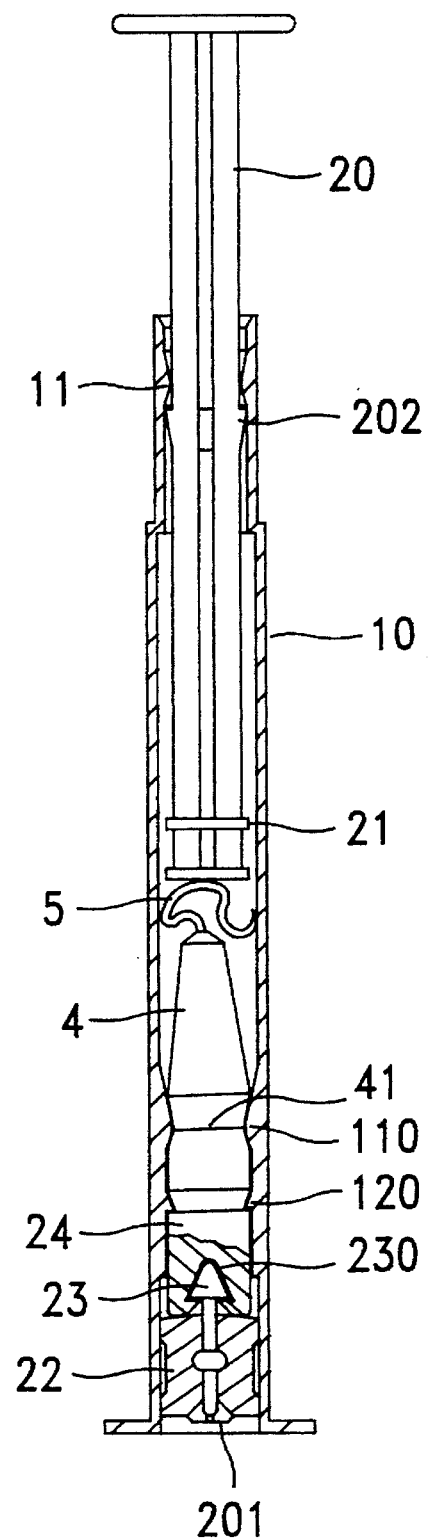
FIG. 7 shows the plunger inserted into the barrel from the front end, and the needle cannula deformed according to the present invention.

Referring to Figures from 4 to 7, when the movable rubber stopper 22 is moved forwards by the plunger 20 to squeeze liquid medicine out of the needle cannula 5 into the body of the patient, the arrowhead-like retainer rod 23 is simultaneously forced into engagement with the conical retaining hole 230 of the locating stopper 24 (see FIG. 4). When the plunger 20 is pulled backwards after injection, the locating stopper 24 with the locking tip 4 and the needle cannula 5 are simultaneously pulled backwards to the inside of the stepped barrel 10. Because the conical retaining hole 230 is made sloping from the longitudinal axis of the locating stopper 24 in one direction, the needle cannula 5 is tilted slightly when the locating stopper 24 with the locking tip 4 and the needle cannula 5 are pulled to the inside of the stepped barrel 10 (see FIG. 5). When the annular locating groove 41 of the locking tip 4 is moved to the position between the second inside annular flange 110 and the third inside annular flange 120, the breaking neck 201 is disposed at the orifice of the rear end of the stepped barrel 10 (see FIG. 5). At the same time, the locking tip 4 is stopped from backward movement by the third inside annular flange 120, and therefore the locking tip 4 and the needle cannula 5 is completely received inside the stepped barrel 10. The plunger 20 is then turned sideways to break the breaking neck 201 of arrowhead-like retainer rod 23 and to disconnect from the arrowhead-like retainer rod 23 (see FIG. 6). The plunger 20 is then inserted into the barrel 10 from the front end to damage the needle cannula 5 (see FIG. 7). Because the needle cannula 5 tilts in one direction when it is moved back to the inside of the stepped barrel 10, it can be easily squeezed into a curved configuration when the plunger 20 is inserted into the stepped barrel 10 from the front end. When the plunger 20 is inserted into the stepped barrel 10 from the front end, the tapered flange 202 is forced into engagement with first inside annular flange 11 of the stepped barrel 10 to stop backward movement of the plunger 20. Furthermore, because the plunger 20 has two collars 21 near the front end, when the needle cannula 5 pierces one collar 21 during the insertion of the plunger 20 into the barrel 10 from the front end, the second collar 21 is still effective for squeezing the needle cannula 5 and deforming it.

It is to be understood that the drawings are designed for purposes of illustration only, and are not intended as a definition of the limits and scope of the invention disclosed.

I claim:

1. A safety minute dose hypodermic syringe comprising a barrel having a front and and a rear end, a locking tip partially inserted into said front end of said barrel to hold a needle cannula, a locating stopper mounted inside said front end of said barrel and fixedly connected to said locking tip, a plunger inserted into said barrel from said rear end of said barrel, and a movable rubber stopper connected to said plunger and moved by said plunger to squeeze liquid medicine out of said barrel through said locating stopper and said needle cannula, wherein: said barrel comprises a first inside annular flange at said front end of said barrel, a second inside annular flange and a third inside annular flange at said rear end of said barrel, an inner diameter of said front end of said barrel being slightly smaller than an inner diameter of said rear end thereof, said second inside annular flange being to limit forward stroke of said plunger; said locking tip is partially inserted into said front end of said barrel and retained in place by said first inside annular flange of said barrel; said locating stopper has a retaining hole at a rear end thereof remote from said locking tip; said movable rubber stopper has a retainer rod longitudinally disposed at center and connected to said plunger for engagement with said retaining hole of said locating stopper, said retainer rod having a breaking neck adjacent to said plunger; said retainer rod of said movable rubber stopper is forced into engagement with said retaining hole of said locating stopper after the injection, for permitting said locating stopper, said locking tip and said needle cannula to be pulled backwards to an inside of said barrel by said plunger through said movable rubber stopper and said retainer rod, so that said locking tip can be retained inside said barrel by said second inside annular flange and third inside annular flange of said barrel, and said plunger can be disconnected from said movable rubber stopper by breaking said breaking neck of said retainer rod, and then inserted into said front end of said barrel to deform said needle cannula.

2. The safety minute dose hypodermic syringe of claim 1 wherein said retaining hole of said locating stopper is made of arrowhead-like shape sloping in one direction from a longitudinal center axis of said locating stopper.

3. The safety minute dose hypodermic syringe of claim 1 wherein said retainer rod is made of arrowhead-like shape for engagement with said retaining hole of said locating stopper.

4. The safety minute dose hypodermic syringe of claim 1 wherein said plunger has at least one collars at one end adjacent to said movable rubber stopper for deforming said needle cannula when it is disconnected from said retainer rod and inserted into said front end of said barrel.

5. The safety minute dose hypodermic syringe of claim 1 wherein said plunger has a tapered flange around a periphery for engagement with said second inside annular flange of said barrel to limit a forward stroke of said plunger.

\* \* \* \* \*